US012018264B2

(12) United States Patent
Shasany et al.

(10) Patent No.: US 12,018,264 B2
(45) Date of Patent: Jun. 25, 2024

(54) METHOD FOR INCREASING VIRIDIFLOROL CONTENT IN TISSUES

(71) Applicant: COUNCIL OF SCIENTIFIC AND INDUSTRIAL RESEARCH, New Delhi (IN)

(72) Inventors: Ajit Kumar Shasany, Uttar Pradesh (IN); Pallavi Yadav, Uttar Pradesh (IN); Shubhra Rastogi, Uttar Pradesh (IN); Syed Uzma Jalil, Uttar Pradesh (IN); Rajendra Singh Bhakuni, Uttar Pradesh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 176 days.

(21) Appl. No.: 17/226,283

(22) Filed: Apr. 9, 2021

(65) Prior Publication Data

US 2021/0403827 A1 Dec. 30, 2021

(30) Foreign Application Priority Data

Jun. 24, 2020 (IN) ............................ 202011026675

(51) Int. Cl.
*C12N 9/88* (2006.01)
*C12N 15/82* (2006.01)

(52) U.S. Cl.
CPC .......... *C12N 15/8243* (2013.01); *C12N 9/88* (2013.01)

(58) Field of Classification Search
None
See application file for complete search history.

(56) References Cited

PUBLICATIONS

GenBank (2001) AJ311872.1. https://www.ncbi.nlm.nih.gov/nucleotide/AJ311872.1?report=genbank&log$=nuclalign&blast_rank=1&RID=SFK2M607013.*
Crocoll et al (2010). Plant Mol Biol. 73:587-603.*
Chen et al (2011). The Plabt Journal.66:212-229.*
Dwevedi et al. 2004. Essential oil composition of different accessions of *Mentha Xpiperitta* L. grown on the northern plains of India. Flavour and Fragrance Journal. 19:437-440.*

* cited by examiner

*Primary Examiner* — Anne Kubelik
(74) *Attorney, Agent, or Firm* — Blank Rome LLP

(57) ABSTRACT

The present invention relates to the development of high viridiflorol containing variety for enhancing the aroma as well as medicinal properties of *Mentha piperita* by overexpressing MPTPS4 gene through genetic transformation. This transgenic plant possesses better growth and able to produce essential oil with good quality contains high viridiflorol maximum of about 25% and proportionate decrease in menthone, menthofuran and menthol of *Mentha piperita* as compared to other control genotype. *Mentha piperita* (CIM-madhuras) that produces viridiflorol, a molecule of potential demand in perfumery, cosmetics, toiletries, drugs and sanitation products.

4 Claims, 1 Drawing Sheet

Specification includes a Sequence Listing.

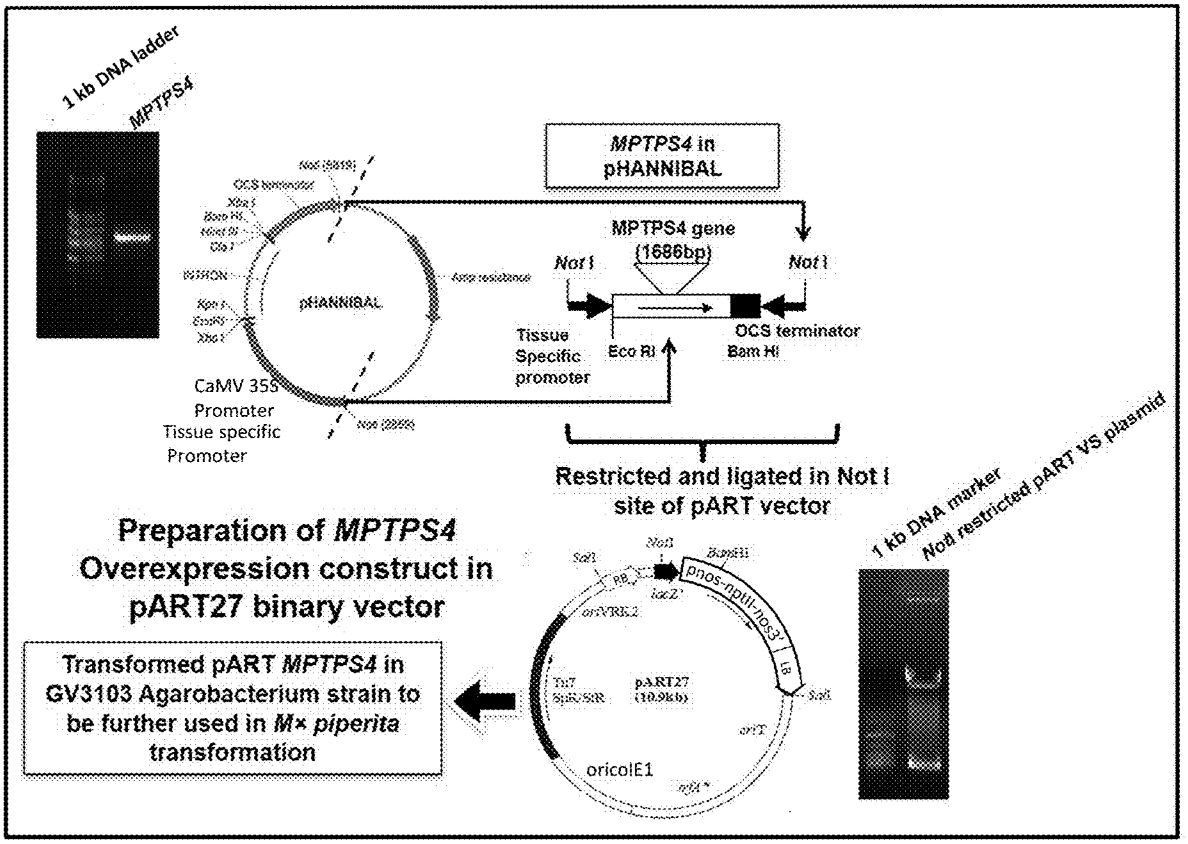
1 kb DNA ladder
MPTPS4
MPTPS4 in pHANNIBAL
pHANNIBAL
OCS terminator
INTRON
Amp resistance
CaMV 35S Promoter Tissue specific Promoter
MPTPS4 gene (1686bp)
Not I
Not I
Tissue Specific promoter
Eco RI
OCS terminator
Bam HI
Restricted and ligated in Not I site of pART vector
1 kb DNA marker
NotI restricted pART VS plasmid
Preparation of MPTPS4 Overexpression construct in pART27 binary vector
Transformed pART MPTPS4 in GV3103 Agarobacterium strain to be further used in M× piperita transformation
pnos-nptII-nos3'
pART27 (10.9kb)
oricolE1

METHOD FOR INCREASING VIRIDIFLOROL CONTENT IN TISSUES

CROSS-REFERENCES TO RELATED APPLICATIONS

This application claims the benefit of priority under 35 U.S.C. § 119 to Indian Patent Application 202011026675, filed Jun. 24, 2020, which application is hereby incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Jun. 7, 2021, is named 217119-SeqList-6-7-2021.txt and is 45,056 bytes in size.

TECHNICAL FIELD

The present invention relates to a method for increasing viridiflorol content in tissues by overexpressing MPTPS4 through genetic transformation. This cultivar possesses better vegetative growth and is able to produce essential oil with good quality that contains high viridiflorol maximum of about 25% and possesses proportionate decrease in menthone, menthofuran and menthol of *Mentha Piperita* as compared to other control genotype(s).

BACKGROUND

Peppermint, *Mentha piperita* belongs to the family Lamiaceae. It is a natural hybrid between spearmint (*Mentha spicata*) and water mint (*Mentha aquatica*). The essential oil of Peppermint extracted via hydro-distillation method from the leaves and used in cosmetics, medicines etc. The essential oil is a mixture of terpenoids in varied proportions, and significantly finds application within the flavour or pharmaceuticals and oral medicative preparations. Comparatively small amounts of sesquiterpenes found in peppermint oil, thus there is an enormous gap within the area of sesquiterpene biosynthesis in genus *Mentha* that is very valuable and plays role in aroma value of oil. The main interest of terpene research is due to their diverse applications and utility with high market values in flavors and fragrances, medicines, industrial chemicals, and agricultural chemicals. Although, there is an immense demand for specific terpenes but the natural producers like plants and microbes synthesize terpenes/terpenoids/phenylpropenes/benzenoids in minute quantities. Chemical synthesis of these molecules is a costly and inefficient process. In addition, chemical synthesis leads to the formation of enantiomeric mixtures, adding problem and difficulties for separation and purification of desired molecule. Hence, with the ongoing efforts, there is also a need to explore new ways to enhance the production of these valuable classes of molecules. Viridiflorol is found to possess a green floral smelling aroma and possess anticarcinogenic and antitumorigenic properties but occurs in plants in very low amount. Supply of this molecule is limiting as these plants only grow in alpine region/endangered/difficult to multiply. Keeping in minds the importance of viridiflorol, the need for developing better plant type containing high viridiflorol content in essential oils of peppermint. In this invention an overexpression construct for the MPTPS4 under the tissue specific promoter mainly the trichome specific promoter (Limonene synthase) was designed as the essential oil is predominantly synthesized and sequestered in the glandular trichomes in *Mentha Piperita* and a maximum of about 25% viridiflorol could be obtained in the overexpressed transgenic plants & in heterologous system.

Objectives of the Invention

The main objective of the invention is to provide a method for obtaining tissues with high viridiflorol content to improve commercial value in terms of aroma as well as enhanced therapeutic properties.

Another objective of the present invention is isolate a sesquiterpene synthase (MPTPS4) gene from *Mentha piperita* and characterize functionally.

Yet another objective of the present invention is cloning and gene expression of MPTPS4, protein isolation and testing for conversion of Farnesyl di-Phosphate (FPP) to viridiflorol.

Yet another objective of the present invention is NMR analysis for confirmation of product of MPTPS4.

Still another objective of the present invention is validation of overexpression of transgenic plants by real time analysis and Gas chromatography-mass spectrometry (GC-MS).

SUMMARY OF THE INVENTION

Accordingly, the present invention provides a method for increasing viridiflorol content in tissues for improved commercial value in terms of aroma as well as enhanced therapeutic properties, as new class of compound will also add the aroma to the leaf of the plant and oil as compared to the non-transformed plants.

In an embodiment, a method for increasing viridiflorol content in tissues is provided. The method comprising:

a.) isolating sesquiterpene synthase gene (MPTPS4) from *Mentha piperita* having SEQ ID NO: 4;

b.) cloning of gene MPTPS4 obtained at step (a) into pHANNIAL vector to obtain a cassette with SEQ ID NO: 8;

c.) re-cloning the cassette obtained at step (c) into pART27 binary vector system with SEQ ID NO: 9; and d.) transforming the vector obtained at step (c) into *Agrobacterium tumerfaciens* for overexpression of MPTPS4.

In another embodiment, a method for increasing viridiflorol content in tissues is provided, wherein the terminator sequence is an octapine synthase (OCS) terminator sequence is set forth in SEQ ID NO: 10.

In another embodiment, a method for increasing viridiflorol content in tissues is provided, wherein the promoter sequence is a tissue specific promoter (Limonene synthase, 797 bp) sequence is set forth in SEQ ID NO: 7.

In another embodiment, a product obtained by the method of the invention is provided.

The product obtained has increased viridiflorol content and is useful for perfumery, cosmetics, toiletries, drugs and sanitation products.

In another embodiment, a transgenic plant obtained by the method of the invention is provided. The plant obtained has increased viridiflorol content and is useful for products related to perfumery, cosmetics, toiletries, drugs and sanitation products.

The present inventors found that overexpression of (MPTPS4) produces high value viridiflorol synthase in *Mentha* under a glycosyltransferase (GTS) specific promoter. According to (Albert-Puleo, 1980, J. Ethnopharmacol. 2,337-344), *Melaleuca quinquenervia* (MQV) essential oil is rich in viridiflorol and could be applied to the whole body as it possesses male and female hormonal balancing properties which were mainly due to viridiflorol. The main attraction of overexpressing viridiflorol like molecule in *Mentha Piperita* is to enhance the medicinal properties as well as the aroma value of the plant. Viridiflorol possesses anticarcinogenic and antitumorigenic properties but occurs in plants in very low amount. The viridiflorol content is found to be higher in plants at higher altitudes. In this investigation an overexpression construct for the MPTPS4 under the tissue specific promoter mainly the trichome specific promoter (Limonene synthase) was designed as the essential oil is predominantly synthesized and sequestered in the peltate glandular trichomes in *Mentha piperita*. Viridiflorol is reported in essential oils of *Mentha piperita* up to (0.1-0.6%). In present invention, a maximum of about 25% viridiflorol could be obtained in the overexpressed the cells and tissues of the transgenic plants. This may be due to the trichome specific promoter which directs the expression of viridiflorol synthase gene in the glandular trichome, the active biosynthesis site and store house of terpenes.

Introduction of 4S-limonene synthase from *Mentha spicata* into *Mentha arvensis* and *Mentha piperita* quantitative and qualitative alterations were observed in monoterpenes pool in both species. Improvement of aroma and flavour in agricultural products by metabolic engineering is not sufficiently utilized. Overexpression of MPTPS4 in *Mentha piperita* increased the viridiflorol content up to 25% compared to 0.1-0.6% in cells and tissues of vector control plant. As observed in 5.4, Km of MPTPS4 is very low and hence utilizes the FPP pool in GTs efficiently. The utilization of FPP might have pulled the precursors IPP and GPP into the pool of FPP resulting into decreased supply of precursor to the monoterpene pathway. This present invention is not limited to the proportionate decrease in menthone, menthofuran and menthol but detected with the increase in viridiflorol. Further, similar pattern of increase in the content of the sesquiterpene alloaromadendrene like viridiflorol observed in all overexpressed lines. This may be due to the fact that increase in viridiflorol concentration might have been an advantage for some enzyme not necessarily biosynthesizing aromdendrene molecules but responsible for other function, to accept viridiflorol as a substrate (high Km) to convert a minor amount to Aromadendrine like molecules. Hence, though higher than control, the concentration of alloaromadendrine is very less in the transgenic plants for viridiflorol synthase.

BRIEF DESCRIPTION OF THE DRAWINGS

FIG. 1 is schematic representation of preparation of overexpression construct.

BRIEF DESCRIPTION OF THE TABLES

Table 1 is viridiflorol analysis in essential oil of transgenic *Mentha* plants over expressing MPTPS4. Values are represented as mean±SD (n=3 biological replicates), VC: Vector.

Table 2 is a comparative analysis of other metabolites in MPTPS4 overexpressing lines of *Mentha* in GC-MS (values are shown in percentage).

DETAILED DESCRIPTION OF THE INVENTION

The present invention will be illustrated in the following examples, which are in no way intended to limit the scope of the present invention.

Example 1

Expression of MPTPS4 Gene

1. Selection of Genes to be Used

Comparative Transcriptome Analysis of *Mentha piperita* and *M. spicata*

To investigate the terpene synthesis pathway of *Mentha Piperita* recently constructed the *Mentha piperita* transcriptome through RNA sequencing of the GT's rich tissue the transcriptomes are deposited at NCBI under the accession no. SRP056511) (Akhtar, 2017 Physiologia *Plantarum,* 160: 128-141) and compared with transcriptome of the GT's rich tissue of *Mentha spicata* (the transcriptomes are deposited at NCBI under the accession No. SRP056511) (Jin, 2014, BMC Plant Biology, 14).

In Silico Analysis of Database Sequences for TPSs Genes

In order to identify the valuable terpene synthase (TPS) genes, Plant trichrome EST database of *Mentha piperita* was mined to retrieve all the TPSs related transcripts/genes. Further, a local Basic Local Alignment Search Tool (BLAST®) of these ESTs was carried out against the transcriptome database of *Mentha piperita*. This led to the identification of some uncharacterized TPS related genes. Based on nucleotide and amino acid sequences, partial ESTs were shortlisted and used to obtain full-length genes for further characterization.

Transcriptome Sequencing and Assembly

The sequncing of paired end cDNA library of transcriptome from trichomes of *Mentha piperita* and *M. spicata* generated a total of 412,458,248 (412.46 million) raw reads for *Metha piperita* and 320,383,922 (230.38 million) raw reads for *M. spicata*. Out of which, number of paired end reads were 143,546,248 (143.5 million) for *Mentha piperita* and 81,145,014 (81.1 million) for *M. spicata*. Snce, paired end sequencing generates high quality alienable sequence data and is more likely to align to a reference; these reads were used for further processing.

Assembly of Transcripts Showing Differential Expression

Transcripts from the libraries of both *Mentha piperita* and *Mentha spicata* were clustered using CD-HIT EST tool applying the criterion of sequence identity threshold as 0.8 for obtaining the set of non-redundant transcripts. A total of 52321 transcripts were obtained both from *Mentha piperita* and *M. spicata* out of which, 16138 transcripts were exclusive to *Mentha piperita* while, 896 transcripts were exclusive to *Mentha spicata* and 35287 transcripts were common in both *Mentha piperita* and *Mentha spicata* (456 up-regulated; 438 down-regulated and 34393 neutral with respect to *Mentha piperita*).

Functional Annotation and GO Classification

Annotations of all the unique transcripts (>300 bp) was performed using a BLASTx homology search against TAIR Database. BLAST hits with e-value scores ≤0.001 were considered as annotated homologous proteins. Transcripts were subjected to Gene Ontology (GO) classification in order to categorize them under the three categories of biological process (BP), molecular function (MF) and cellular component (CC). Out of the total 52321 transcripts in both plants, 36793 transcripts got annotated with different GO terms in aforementioned three categories of BP, MF and CC. The order of the GO term assignment was CC (68.61%) >MF (21.43%)>BP (9.94%).

Example 2

Identification of Transcripts Related to Terpene Synthases

To explore the array of terpenoids, it was important to identify the transcripts related to the terpene synthases. 89 and 82 TPS transcripts were identified in *Mentha piperita* and *Mentha spicata*, respectively when annotated against the TAIR database of *Arabidopsis* shows number of transcripts for each gene identified in the annotation.

TABLE 1

| SAMPLE | MARCH | APRIL | MAY | JUNE | JULY |
|---|---|---|---|---|---|
| MPOT_1 | 8.66 +/− 0.0049 | 7.86 +/− 0.0015 | 8.71 +/− 0.0058 | 8.75 +/− 0.0025 | 7.65 +/− 0.0164 |
| MPOT_2 | 25.98 +/− 0.0043 | 26.6 +/− 0.0045 | 25.2 +/− 0.0248 | 21.7 +/− 0.0341 | 24.43 +/− 0.0285 |
| MPOT_3 | 20.40 +/− 0.0029 | 22.5 +/− 0.0038 | 19.2 +/− 0.0494 | 22.7 +/− 0.0107 | 15.14 +/− 0.0049 |
| MPOT_4 | 14.53 +/− 0.0013 | 14.8 +/− 0.0065 | 14.2 +/− 0.0235 | 11.3 +/− 0.0198 | 12.43 +/− 0.0071 |
| VC | 0.40 +/− 2.30 | 0.56 +/− 0.0004 | 0.53 +/− 0.0001 | 0.54 +/− 6.67 | 0.42 +/− 0.0004 |

TABLE 2

| Compound name | MPOT_1 | MPOT_2 | MPOT_3 | MPOT_4 | Vector |
|---|---|---|---|---|---|
| α-Pinene | 0.59 | 0.54 | 0.58 | 0.60 | 0.69 |
| β-Pinene | 1.44 | 1.23 | 1.32 | 1.38 | 1.61 |
| D-Limonene | 5.70 | 4.88 | 5.23 | 5.48 | 6.47 |
| Linolool | 0.21 | 0.18 | 0.19 | 0.20 | 0.23 |
| Menthone | 23.7 | 20.2685 | 21.95 | 22.924 | 27.394 |
| Menthofuran | 17.75 | 15.03 | 16.14 | 16.80 | 20.12 |
| Menthol | 18.95 | 16.14 | 17.36 | 18.16 | 21.71 |
| α-Terpineol | 0.66 | 0.59 | 0.62 | 0.65 | 0.78 |
| Pulegone | 3.38 | 2.89 | 3.17 | 3.29 | 3.97 |
| Menthyl acetate | 3.426 | 2.911 | 3.154 | 3.2865 | 3.93 |
| β-Bourbonene | 0.10 | 0.09 | 0.09 | 0.11 | 0.12 |
| Caryophyllene | 3.04 | 2.59 | 2.79 | 2.93 | 3.47 |
| β-Cubebene | 0.13 | 0.11 | 0.12 | 0.12 | 0.15 |
| Alloaromadendrene | 0.28 | 0.54 | 0.39 | 0.28 | 0.02 |
| Humulene | 0.19 | 0.16 | 0.17 | 0.18 | 0.21 |
| cis-β-Farnesene | 0.38 | 0.34 | 0.35 | 0.35 | 0.38 |
| Germacrene D | 0.73 | 0.63 | 0.69 | 0.71 | 0.86 |
| γ-Muurolene | 0.12 | 0.10 | 0.10 | 0.11 | 0.13 |
| Viridiflorol | 7.77 | 26.03 | 21.94 | 14.38 | 0.585 |

Pathway Analysis (Differentially Expressed)

MVA and MEP Pathway

Differential expression profile of transcripts annotated as MVEP and MVA pathway genes showed that the transcripts of genes involved in MVEP pathway namely CMK, DXR, DXS, MCT, MCS, HDR and GGPP are upregulated in *Mentha spicata* and MVA pathway transcripts namely AACT, HMGS, WVK, PMK, PMD and FPP are downregulated compared to the reference gene ACT (Actin).

Terpene Synthases

In the differential gene expression analysis, a total of 94 TPS transcripts were found, out of which, 12 were up-regulated, 9 were down-regulated and 44 were neutral in *Mentha spicata* when compared to *Mentha piperita*, while 11 TPS transcripts were exclusively expressed in *Mentha piperita* and 18 were in *Mentha* spicata.

Analysis of Available *Mentha piperita* Trichome EST Database for Terpene Synthase ESTs analysis of the Plant trichOME database revealed the presence of about eight different TPS ESTs.

Example 3

Identification, Isolation and Sequence Characterization of the TPSs in *Mentha* piperita A local BLAST of 45 ESTs from Plant trichOME database was performed against transcriptome database of *Mentha piperita*. Out of these 11 ESTs which were found less annotated to the database were used to get full-length genes. RACE primers were designed from the available TPS partial sequences to obtain full-length genes. A total of six genes namely MPTPS1 with SEQ ID NO: 1; MPTPS2 with SEQ ID NO: 2; MPTPS3 with SEQ ID NO: 3; MPTPS4 with SEQ ID NO: 4; MPTPS6 with SEQ ID NO: 5 and MPTPS7 with SEQ ID NO: 6 were cloned from *Mentha piperita*. All the genes were amplified from the cDNA of trichome rich tissue of *Mentha piperita* (CIM-Madhuras), cloned, sequenced and characterized. The sequences obtained were subjected to BLASTx and BLASTn analysis. The amino acid sequence of *Mentha piperita* was compared to ones existing in the NCBI database for the identification of signature sequences/motifs and or domains.

Out of these six terpene synthases, four (MPTPS1, MPTPS2, MPTPS3, and MPTPS4) are sesquiterpenes and two (MPTPS6 and MPTPS7) are monoterpenes. In sesquiterpenes, MPTPS3 and MPTPS4 showed less identity to others from the database after BLASTx analysis, therefore, MPTPS3 and MPTPS4 were considered for further analysis and characterization.

MPTPS3 and MPTPS4 Gene Expression in Different Tissues.

Comparison of the deduced amino acid sequences of MPTPS3 and MPTPS4 showed 81% similarity. Tissue-specific expression was analyzed for MPTPS3 and MPTPS4 in different tissues in *Mentha piperita* for comparison. MPTPS4 showed significantly higher spacial expression than MPTPS3 in the order of trichome>leaf>stem>root. Hence, only MPTPS4 was taken into consideration for the further downstream functional characterization.

MPTPS4

EST of MPTPS4 was extracted from the plant trichOME EST database of *Mentha piperita* annotated as Terpene synthase (Accession no AW255698). The partial sequence thus obtained was 628 bp and which was subjected to 3' and 5'RACE in order to get the full-length MPTPS4 gene. Full-length cDNA sequence of MPTPS4 gene was found to be 1686 bp, encoding a polypeptide of 561 amino acid residues. The molecular weight of the deduced protein was predicted to be 65.09 kDa and computed isoelectric point (pI) was 4.91. The nucleotide sequence has been submitted to the NCBI database with the accession number (MH790402). Nucleotide sequences of MPTPS4 from *Mentha piperita* showed 82% similarity with TPS4 of *Origanum vulgare*, while amino acid sequences showed 77% sequence similarity with TPS4 of *Origanum vulgare* which is reported to be a Bicyclogermacrene synthase.

Example 4

Cloning of MPTPS4 Gene in pET28a (+) and Transformation for Bacterial Expression The MPTPS4 gene (~1.6 kb) was sub cloned from pGEM-T Easy cloning vector onto the pET28a (+) expression vector. The positive recombinant plasmid was then transformed 30 into *E. coli* BL21 (DE3) bacterial expression host cell and both the induced and uninduced host proteins were isolated to analyze on the SDS PAGE. 64 kDa MPTPS4 protein was obtained after purification and desaltation from the induced host cell was confirmed by running SDS PAGE and comparing with the protein molecular weight marker.

Enzyme Assay

GC-MS Analysis

The recombinant MPTPS4 protein was produced in *E. coli* BL21 (DE3), enzyme assay reactions were set up with crude extracts in which extract was incubated with FPP and the product was analyzed in GC, a unique peak of viridiflorol was observed when compared to the vector control. Similarly, purified MPTPS4 protein was incubated with enzyme substrates FPP, GPP and GGPP and the reaction products were analyzed using GC-MS. The reactions in which GPP and GGPP were used as substrates did not show any product formation. On the other hand, when FPP was used as the substrate of MPTPS4 protein, a product peak was generated. The product was identified to be "Viridiflorol" based on the mass spectra similarity as per the NIST library.

Enzyme Kinetics

The purified recombinant MPTPS4 enzyme was characterized for their catalytic activities with FPP. Rate of reaction for different substrate (FPP) concentration (0-350 μM) (was also analyzed). The amount of substrate converted in each reaction was calculated, and the amount of enzyme was standardized to micromole per minute per microgram. The reaction rate per microgram enzyme per second was established, and the reaction rate (1/second) was calculated.

Product Confirmation of MPTPS4 Through NMR Studies

Structural Analysis of MPTPS4 Product

The expression construct pET28a-MPTPS4 was introduced into *E. coli* BL21-CodonPlus (DE3) cells together with plasmid Add gene Plasmid 35150: pBbA5c-MevT-MBIS, for the utilization of FPP as the substrate, were grown in LB medium and the product extracted was 25.2 mg. This product was subjected to $^{1}$H-nuclear magnetic resonance spectrometry, $^{13}$C NMR and DEPT 135 spectrum. The $^{1}$H and $^{13}$C chemical shift of viridiflorol is shown in GC-MS and TLC analysis.

Example 5

Preparation of Over Expression Construct of MPTPS4

The MPTPS4 (1686 bp) gene with SEQ ID NO: 4 was cloned in pHANNIBAL vector system by replacing the PDK intron to yield phannibal-MPTPS4, under tissue specific promoter (Limonene synthase, 797 bp) with SEQ ID NO: 7. The whole cassette (~3.5 kb) SEQ ID NO: 8 was cloned into pART27 binary vector system with SEQ ID NO: 9 and confirmed by restriction analysis. The binary vector with and without the genes were then transformed into GV3103 strain of *Agrobacterium tumefaciens* separately, positive clones selected on kanamycin antibiotic plates and confirmed with the help of colony PCR.

Generation of Transgenic *Mentha* Lines of MPTPS4

In vitro maintained *Mentha* plants in the laboratory were used for *Agrobacterium* mediated internode transformation for generating transgenic plants. All individual transformation experiments were accompanied with vector control. PART-MPTPS4 transformed internode was placed on selective MSB_M media. After 3-4 weeks, direct regeneration was induced as a result of pART-MPTPS4 gene transformation on kanamycin (50 mg $L^{1}$) selection medium.

Analysis of Transgenic *Mentha* Plants

PCR analysis was carried out to confirm the transfer of transgene cassette into the transgenic lines. Genomic DNA was extracted from each putative transgenic line and PCR analyzed using primers of npt II gene. Four lines of pART-MPTS4 exhibited an amplification of 750 bp, which was absent in the no template control lane, hence were confirmed to be transgenic lines.

Overexpression Studies Through Quantitative Expression

Four independent kanamycin-resistant *Mentha piperita* transformants of pART-MPTPS4 (MPOT_1, MPOT_2, MPOT_3 and MPOT_4) and pART only (Vector Control, VC) transformants were grown in green house. The expression levels of the transgenic lines were determined by quantitative RT-PCR. Overexpression in four independent transgenic lines was in order of MPOT_2 (18.9-37.7 fold) >MPOT_3 (13.4-26.4-fold)>MPOT_1 (9.4-25 fold) >MPOT_4 (5.4-16.0 fold) compared to the vector control. The range denotes in planta fold expression as estimated from the isolated mRNA during March to July.

Overexpression Analysis Through GC-MS

In order to study the effect of increased MPTPS4 expression on the content of plant essential oils, four transgenic (MPOT_1, MPOT_2, MPOT_3 and MPOT_4) plant lines produced through *Agrobacterium* transformation were grown in a greenhouse and essential oil profiles for all these lines were generated using GC-MS. All the four MPTPS4 over-expressed transgenic lines exhibited significant increase in viridiflorol content compared to the vector control. The range denotes in planta fold expression as estimated from the isolated mRNA during March to July.

Correlation of Metabolite Synthesis with Gene Expression

To see the effect of MPTPS4 overexpression on the other metabolites, comparative analysis was performed through GC-MS and values (%). All the four MPTPS4 overexpressing transgenic lines exhibited increase in the viridiflorol content while, other metabolites like menthone, menthofuran and menthol decreased as flux diverted towards increased content of viridiflorol as well as one sesquiterpene, alloaromadendrene also increased compared to control plants.

Subcellular Localisation of the MPTPS4

N-terminal in-frame GFP fusions were made with the MPTPS4 full-length coding regions in the p326-SGFP vector between the XbaI and BamH I restriction enzyme sites to create p326-MPTPS4/SGFP. GFP fluorescence for full-length p326-MPTPS4/SGFP coding regions was observed as a diffused signal exclusively in the cytosol. Expression of a control GFP construct was also localized in the cytoplasm. These results confirm the predicted cytosolic localization of the enzyme.

Procurement Details of all the Biological Materials Used in Invention

*Mentha* plants: The germplasm accessions of *Mentha piperita* cv. 'Cim-Madhuras' was obtained from National gene Bank for medicinal and Aromatic Plants (NGBMAP) maintained at Central Institute of medicinal and Aromatic Plants (sponsored by Department of Biotechnology, Regime of India) in Lucknow (26.5° N, 81.010 E), India.

Bacterial Host Strains

| Strain | Description | Reference |
|---|---|---|
| *Escherichia coli* (DH5α) | *supE44* Δ *lacU*169 (φ80 *lacZ* Δ M15) hsd R17 *rec* Al *end*Al*gyr*A96 *thi*-1 *rel* A1 | Sambrook et al., 1989 |
| *Escherichia coli* BL21 Star ™ (DE3) | $F^-$ *ompT hsd*$S_B$($r_B^-$ $m_B^-$) *gal dcm lacY1* (DE3) | Novagen www.novagen.com |
| *Agrobacterium tumefaciens* (GV3103) | Resistance for gentamycin and rifampicin antibiotics | Intact Genomics www.intactgenomics.com |

Vectors

| Plasmid vectors | Description | Source |
|---|---|---|
| pGEM ®-T | 3.0 kb in size, multiple cloning sites having 15 unique restriction sites, LacZ fragment, pUC/M13 forward and reverse priming sites, T7 and SP6 promoter/primer binding site, fl origin, T7 RNA polymerase transcription initiation site and has ampicillin resistance ORFs. | Promega www.promega.com |
| pET 28a(+) | 5.369 kb, N-terminal His•Tag ® configuration with an optional C-terminal His•Tag sequence, f1 origin of replication, T7 promoter, T7 terminator, lacI coding sequence, kan coding sequence, f1 origin replication. | Novagen www.novagen.com |
| pHANNIBAL | 5.824 kb in size with bacterial ampicillin resistance is designed for directional insertion of PCR products on either side of the PDK intron. | CSIRO www.pi.csiro.au |
| pART 27 | Size of 11.667 kb, RK2 minimal replicon for maintenance in *Agrobacterium*, the ColE1 origin of replication, Tn7 spectinomycin/streptomycin resistance gene as a bacterial selectable marker, nos promoter, nos terminator, LacZ fragment | CSIRO www.pi.csiro.au |
| p326-sGFP | 4.488 kb in size, CaMV35S promoter, nos terminator, ampicillin resistance, 900 bp sGFP genes cloned between the promoter and terminator. | Provided by Inhwan Hwang (POSTEC, Korea) |
| pBbA5c | 1.3264 kb in size, lacUV5 promoter, rrnB terminator, chloroamphinicol resistance, low copy. | Addgene https://www.addgene.org |

pART-MPTPS4: —The MPTPS4_sense gene (500 bp) and MPTPS4_antisense gene (500 bp) were subcloned from pGEM-T Easy cloning vector onto the pHANNIBAL cloning vector under tissue specific promoter by replacing cauliflower mosaic virus (CaMV) 35S promoter with octopine synthas (ocs) terminator with SEQ TD NO: 10, sequentially on either side of the intron between EcoRI/KpnI and XbaI/HindIII restriction enzyme sites respectively to get the two arms of the hairpin which was confirmed by restriction analysis using the XhoI and XbaI, the first and the last restriction enzyme sites of multiple cloning sites, MCS1 and MCS2 of pHANNIBAL respectively. The hairpin cassette was then cloned into a pART 27 binary vectors in a single step using the Not I restriction sites as there are two NotI restriction enzyme sites in pHANNIBAL and a single site in pART27 binary vector.

cDNA of trichome rich tissue of *Mentha piperita* (CIM-Madhuras):—cDNA of trichome rich tissue of *Mentha piperita* were isolated in Dr. Ajit K. Shasany's Lab, Biotechnology Division, CSIR-CIMAP, Lucknow, India.

Kanamycin-resistant *Mentha piperita* transformants of pART-MPTPS4 (MPOT_1, MPOT_2, MPOT_3 and MPOT_4):—To prepare the overexpression construct of the MPTPS4, specific primers with SEQ ID NO: 11 and SEQ ID NO: 12 were designed introducing BamHI with and EcoRI with restriction enzyme sites by replacing the PDK intron into pHANNIBAL vector system to yield pHANNIBAL-MPTPS4 under tissue specific promoter by replacing cauliflower mosaic virus (CMV) 35s promoter with octapine synthase (OCS) terminator. The cloned fragments were confirmed by restriction analysis and sequencing. The whole cassette with promoter, gene and terminator was then cloned into pART27 binary vector system. The cloned fragments were confirmed by restriction analysis. Binary vector with and without the transgene (MPTPS4) was then transformed into GV3103 strain of *Agrobacterium* separately.

Generation of transgenic *Mentha* lines of MPTPS4—In vitro maintained *Mentha* plants in the laboratory were used for *Agrobacterium* mediated internode transformation for generating transgenic plant. All individual transformation experiments were accompanied with vector control. PART-MPTPS4 transformed internodes were placed on selective MSB_M media. After 3-4 weeks, direct regeneration was induced as a result of pART-MPTPS4 gene transformation on kanamycin (50 mg $L^1$) selection medium. Four independent kanamycin-resistant *Mentha Piperita* transformants of pART-MPTPS4 (MPOT_1, MPOT_2, MPOT_3 and MPOT_4) and pART only (Vector Control, VC) transformants were obtained and grown in green house. Experiments were performed in Dr. Ajit K. Shasany's Lab, Biotechnology Division, CSIR-CIMAP, Lucknow, India.

Advantages of the Invention

The present invention provides for:

1.) A method for obtaining transgenic plants with high viridiflorol containing variety for enhancing the aroma, therapeutic properties.
2.) A method for enhancing the medicinal properties of *Mentha piperita* by overexpressing MPTPS4 through genetic transformation.
3.) The method provides better vegetative growth.
4.) The method produces plants with essential oil with good quality containing high viridiflorol maximum of about 25%.
5.) The plants obtained with increased viridiflorol content produced by the method of the invention are used in perfumery, cosmetics, toiletries, drugs and other sanitation products.
6.) The produced viridiflorol adds sweetness to the aroma of plant essential oil.
7.) The obtained viridiflorol possess anticarcinogenic and antitumorigenic properties.

REFERENCES

1. Albert-Puleo M (1980) Fennel and anise as estrogenic agents. J Ethnopharmacol 2:337-344.
2. Akhtar M Q, Qamar N, Yadav P, et al (2017) Comparative glandular trichome transcriptome-based gene characterization reveals reasons for differential (−)-menthol biosynthesis in *Mentha* species. Physiologia *Plantarum* 160: 128-141. doi: 10.1111/ppl.12550.
3. Jin J, Panicker D, Wang Q, et al (2014) Next generation sequencing unravels the biosynthetic ability of Spearmint (*Mentha spicata*) peltate glandular trichomes through comparative transcriptomics. BMC Plant Biology 14. doi: 10.1186/s12870-014-0292-5.

SEQUENCE LISTING

```
<160> NUMBER OF SEQ ID NOS: 12

<210> SEQ ID NO 1
<211> LENGTH: 1677
<212> TYPE: DNA
<213> ORGANISM: Mentha piperita
<220> FEATURE:
<221> NAME/KEY: gene
<222> LOCATION: (1)..(1677)
<223> OTHER INFORMATION: The partial sequence thus obtained was 447 bp
      and was incomplete from the 3' region. 3' RACE was carried out to
      convert it into a full-length gene. Full-length cDNA sequence of
      MPTPS1 gene was found to be 1680 bp, encoding a a polypepeptide of
      560 amino acids.
<300> PUBLICATION INFORMATION:
<308> DATABASE ACCESSION NUMBER: MH790399
<309> DATABASE ENTRY DATE: 2018-10-24
<313> RELEVANT RESIDUES IN SEQ ID NO: (1)..(1677)

<400> SEQUENCE: 1

atggctgaaa tctgtgcgtc ggctgctcca atctcaacaa agaatacaag tgtagaggaa     60
```

-continued

```
atcctcgatc ggtaacatat catcccagcg tttggagaga tcattttctt gcatatacta    120

acgacgtcac ggaaatcagt gctgctgaga aggaacaact cggaaagcaa aaggaaaagg    180

ttaagaattt gctactcaaa ctccaaatga ttcaacgctc aagatcgacc tcatcgatgc    240

aatccaacgt ctagggttgg gctatcattt cgaggaggaa atcgacggat ccttgcgaaa    300

aattcgcgac agttatgaaa tgttaagtag caaaggcgag ggcgatgtcc gtgttcttgc    360

tcttcgcttt cgtctgctta gacaacaagg ttatcgcgtc ccatgcgaag tgttcaacaa    420

attggtagac gacgaaggga attttaagga gtcgttgatt aacgacgttg aagggatgct    480

aagcttgtac gaagcttcga attatggaat aaatggagag gaaattatgg acaaagcctt    540

agaatttct tcttctcatc ttgaggattc aatccaaaaa aaacccactt gtctttcgag    600

acgagtgaaa gaagctttgg atatgccgat tagcaagact ttgatgagat tgggagcgag    660

aaaattcata tctatttatg aagaagacga gtcgcataat gaattattat tgaattttgc    720

aaaactggac ttcaatatag tacaaaagat gcatcaaaga gagttgcacc atattacaag    780

gtggtgggaa gatttagact ttaaaagtaa actacctttt gcaagagata gagtggtgga    840

gtgctacttc tggattttgg gagtttattt tgaaccaaaa tacgaaactg caagaagatt    900

actaactaaa gtcatatcca tggcttccat ccttgatgat atatatgatg tttatgggag    960

tttagatgaa ctccgacatt tcaccgatgc tattcaaaga tgggatattg tcggtgctga   1020

agagttgcca ccatacatga gaatatgtta tgaagcttta ctaggtgtat atgccgaaat   1080

ggaagatgaa atggtaaaac aaggccagtc atatcgcata gtctatgcaa aacaggagat   1140

gataaaattg gtgagggcgt atatggaaga ggcggagtgg tgttatagca agtatattcc   1200

aaggatggat gagtatatga aactggcact cgtatccggc gcttacatga tgctatcgac   1260

aacttcttta gtcgggatga tggaagaacc catctcagta cacgattttg attggatcac   1320

cggcgaacca cccatcttac gagctgcatc cgttatttgt aggttgatgg acgacatggt   1380

aggccatggg attgagcaaa aaattacgag cgtggatatt tacatgaggg aaaacgggtg   1440

ctcgaagacg gaagcttttg gagagttttg gaaacgagtg aagaaagcat ggaaggatat   1500

gaatgaggag tgcctggagc caaggccagc atccatgccc atacttactc gagttctcaa   1560

tcttgctcgc gtcatcaatt tattgtacgt tggtgaagat gcctatggta gttcaagtac   1620

taagaccaaa gatttcattc aatccgtgct cgtagatccc ctgcactcaa ctatttg      1677
```

<210> SEQ ID NO 2
<211> LENGTH: 1635
<212> TYPE: DNA
<213> ORGANISM: Mentha piperita
<220> FEATURE:
<221> NAME/KEY: gene
<222> LOCATION: (1)..(1635)
<223> OTHER INFORMATION: The partial sequence obtained was 420 bp and was incomplete from the 3' region. Hence, 3' RACE was carried out to convert it into a full length gene. Full-length cDNA sequence of MPTPS3 gene was found to be 1686 bp, encoding a polypetide of 560 amino acids.
<220> FEATURE:
<221> NAME/KEY: gene
<222> LOCATION: (1)..(1635)
<223> OTHER INFORMATION: The partial sequence thus obtained was of 420 bp which was further subjected to 3' and 5'RACE in order to get the full-length MPTPS2 gene. Full-length cDNA sequence of MPTPS2 gene was found to be 1635 bp, encoding a polypeptide of 545 amino acids.
<300> PUBLICATION INFORMATION:
<308> DATABASE ACCESSION NUMBER: MH790400
<309> DATABASE ENTRY DATE: 2018-10-24

-continued

<313> RELEVANT RESIDUES IN SEQ ID NO: (1)..(1635)

<400> SEQUENCE: 2
atggatattc ctgcaccagt ttcggcttac aacgacgacg ttcgacgctc tgtaacttac 60
catcccaaca tttggggaga cttttttctt gcctatactt cagacttcac ggaaacctcc 120
attgctgaaa aggaagaaca cgaaaggcta aaggaggaga ttaggaaatt gctcctgcaa 180
actgaagatg aatcaacgct gaaattagaa ctcatcgatt cagttcaacg ccttggagta 240
ggctaccatt tccgaaaaga aatcgataca gcgttgcgtt acgttcatga caccaagaac 300
aaggacgatc ttcgtgtagt agctcttcgc tttcgcctcc ttagacaaca tggtttccat 360
gttccttgcg atgtgtttag tgaattcata gacccccaag gaaatttcaa ggagtcgata 420
atcaacgatg ttgaagggat attgagctta tacgaggcat caaattatgg agtgcatgga 480
gaagaaattc ttgacaaagc attaggtttt tgttcatctc gtctcgaatc tttagtcacc 540
gacatgaatg atacttgtct ttcaagacaa gttaaggaag ctttgaagat cccaattagc 600
aagactctaa cgaggttggg agcaagaaag ttcatttcta cgtatcgaga agtcgactca 660
cacaacgaaa aattactcaa ctttgccata ttggacttca acctagtaca aaggctacat 720
cagaatgagc tcagccatct tacaaggtgg tggaaggaat tagactttgc aaataagcta 780
tcttttgcta gagatagact agtggaatac tatttttgga ttgtgggagt ttattttgaa 840
ccgcggttcg gtattgcacg aaaattacta accaaagtca tttatatggc ttccgtcctt 900
gatgacattt acgacgtgta tggaactctg gacgaactaa tgcttttcac gagcattgtt 960
cgaaggtggg acattagtgc tattgatcaa ttgcctgcat acatgagaat atacttgaaa 1020
gccctcttcg atgtgtatgt tgaaatggaa gaagaaatgg gaaagatagg caaatcatac 1080
gcaattgaat atgcaaaaga agagatgaaa agattggcgg agatgtacct tgaagaggca 1140
aaatggtcct ttagcaagta caagcccaca atgcgagagt acatgaaggt ggctctttta 1200
tcatccggtt acatgatgat gacagtaaat tcattagctg ttatcgaaga tgaaattacc 1260
aatgaagagt ttgattgggt tttgagcgaa ccgccaattc taaagtcatc gttgatgatt 1320
acaagattaa tggacgacct tgcaggatat gggtttgaag agaaaaactc agcagtgcat 1380
tactacatga atgaaaaggg cgtgtcggag ggggaagcca ttgcggagtt ccggaaacaa 1440
gtggagaagt catggaagac tctaaacaag gaatgcttag agccaagagc agcctccatg 1500
cccatcctca agtgtgttgt gaattttact cgtgtcatag ttgtgttata cacagatgaa 1560
gatgcatacg gaaattccaa aactaaaacc aaagatatga tcaaatccat actcgttgat 1620
cccctaacag tttag 1635

<210> SEQ ID NO 3
<211> LENGTH: 1686
<212> TYPE: DNA
<213> ORGANISM: Mentha piperita
<220> FEATURE:
<221> NAME/KEY: gene
<222> LOCATION: (1)..(1686)
<223> OTHER INFORMATION: The partial sequence obtained was 420 bp and was incomplete from the 3' region. Hence, 3' RACE was carried out to convert it into a full length gene. Full-length cDNA sequence of MPTPS3 gene was found to be 1686 bp, encoding a polypeptide of 560 amino acids.
<300> PUBLICATION INFORMATION:
<308> DATABASE ACCESSION NUMBER: MH790401
<309> DATABASE ENTRY DATE: 2018-10-24
<313> RELEVANT RESIDUES IN SEQ ID NO: (1)..(1686)

<400> SEQUENCE: 3

-continued

```
atggaaattt attccccagt tgttcctgca actgcaatca aagatgtgaa gaagttgaat     60

gaaattcgaa aatccgccaa attccatcca actatttggg gagactattt tctagcttat    120

aattctgata atacgctaac ctcaaatggc gaagaaaaag aagttgcaaa gcagaaagaa    180

atggtgcgga aactgctagc tgaagcccca gaaaattcca cctacaaaat ggaactcatc    240

gatacaatcc agcgcctggg agtggaatat cattttgaaa aagaaattga aaattcctta    300

aaatatattc ataaaaatta tgtccaccaa aatagtaaag acgacgatcc ccacaccgtg    360

gctcttcgtt ttcgtttgct cagacaacaa ggttacaacg tcccatgcga tgttttccgc    420

aaattcattg atagtgaagg aaattttatg gagtcatcga cagagaacgt tgaaggtttg    480

ttggaattat acgaggcatc gcatctcgcg acacgtggcg aggaaattct gaatagagca    540

atggagtttt gttcttccca tctccaaaca ttagtgaatc agcagttagt agaaaatgtt    600

tctctttcta aacgtgttag cgaagctctg aagatgccaa tttgcaggag tcttacaagg    660

ttgggtgcca gaaagttcat ctctctatac gaagaggatg attcgcacaa tgaaatactt    720

ttgaattttg caaaattgga tttcaatatt gtgcagaaga tgcaccagag agagctcagt    780

gatgctacta ggtggtggaa aaaattggag gtggcgaata aaatgcctta cgcgagagac    840

agaattgtgg agtgcttctt ttggatagtg gggtctact ttgagccatg ctattctatt     900

gcaagaagaa tattaatcaa aagcataagt atggcttcca ttattgatga cacctacgaa    960

tatgcaaccc tagatgaact gcaaattcta actgatgcta ttcaacgttg ggatgttaac   1020

gagacattgg aagattcgcc accgtacatc caaatgtgct acagaagcct tatccaagct   1080

tatgctgaaa tagaagatga agtactgaag aagaactcag aagaatcgta ccgcgtccaa   1140

tatgcaatac aagatatgaa aaaattggtg atggcatatt atgaagaggc gaaatggttg   1200

tacaataata gtattccaac aatggaggaa tatatgaagg tgtcactagt ttcatgtggt   1260

tacatgatgt tgtcaacaac ttctttagtt ggtatgggga ctaatcaagt tagcaaatca   1320

gattttgatt ggattgtaaa tgaacctcta atggttcgag catactcagt aatttgtcga   1380

ctaatggacg acttagtcgg agacgagtat gaggagaagc cgtcgtcggt ccattgttac   1440

atgaagcaat atggaatgtc aaaggaggaa gctcgagctc aactcgaaga acaagtgaaa   1500

ggagcatgga aggatatgaa tgaagaatgc ctcgagccga gaccagcctc gatgcaaatc   1560

cttatgcgcg ctttgaattt tggtcgagtc ataaatcttc tgtatgcaga agacgattgc   1620

tatgccaatc ccattaattc caaagaatgg gtgaagatgg tgcttgttga gcctgttccc   1680

atttga                                                              1686
```

```
<210> SEQ ID NO 4
<211> LENGTH: 1686
<212> TYPE: DNA
<213> ORGANISM: Mentha piperita
<220> FEATURE:
<221> NAME/KEY: gene
<222> LOCATION: (1)..(1686)
<223> OTHER INFORMATION: The partial sequence thus obtained was 628 bp
      and which was subjected to 3' and 5'RACE in order to get the full-
      length MPTPS4 gene. Full-length cDNA sequence of MPTPS4 gene was
      found to be 1686 bp, encoding a polypeptide of 561 amino acids.
<300> PUBLICATION INFORMATION:
<308> DATABASE ACCESSION NUMBER: MH790402
<309> DATABASE ENTRY DATE: 2018-10-24
<313> RELEVANT RESIDUES IN SEQ ID NO: (1)..(1686)

<400> SEQUENCE: 4

atggaaattt attccccagt tgttcctgca atcaaagatg tgaagaggtt ggatgaaatc     60
```

-continued

```
cgaaaatccg ccaaatacca tccaactatt tggggagact tttttctagc gtataattcc    120

gataatacga aaatctctga tggtgaagaa gaagaagttg caaagcagaa agaaatggta    180

cggaaactgc tagctgaagc cccagaaaat tccacctaca aaatggaact catcgataca    240

atccagcgcc tgggagtgga atatcatttt gaaaaagaaa tcgaaatatc cttgaaatat    300

attcatgaga attatgtgca ccaaaacagc aaagacgacg atcttcacac cgtggctctt    360

cgttttcgtt tgcttagaca acaaggttac aacgtcccat gcgacgtttt cagcaaattc    420

accgaccgtg aaggaaattt tgcggcggcg ctgagaaatg acgttgaaag tttgttggaa    480

ttatatgagg cgtcgcatct cgcgacacgt ggcgaggaaa ttctggacag cgcaatggag    540

ttgtgttctt cccatctcca agcattagta aatgatcagc agttggtgaa caatgtttct    600

ctctctaaac gagtgattga agctctgaag atgccaattc gcaagagtct cacgagattg    660

ggtgcgagaa agttcatctc tctataccaa gaggatgatt cgcataatga aatacttttg    720

aattttgcga aattagattt caatatagtg cagaagatgc accagagaga gcttagtgat    780

gctacgaggt ggtggaagaa gttggacgtg gcgaataaaa tgccttacgc aagagacaga    840

aatgtggagt gcttcttttt ggatggtggg cgtctacttc gagcatgcta cgctactgca    900

agaaaaatat tacttaaatg cataagtatg gcttcaatta ttgatgacac ctacgaatat    960

gcaaccctac atgaactgca aattctcacc gacgctatcc aacgttggga tgttaatgag   1020

gcattggagg attcgccacc atatatacaa atgtgctaca gaagccttat tcaaacttat   1080

gttgaaatag aagatgaagt agtggagaaa tttggaggag aatcgtcata ccgtgtccaa   1140

tatgcaatac aagatatgaa aaaatcggtg tgggcatata tggaagaggc gaaatggatg   1200

tatgacgatt atattccaac cgtggaggag tatatgaagg tttcgatcgt atcttgtggt   1260

tatatgacaa tgtcaaccac ttctttagtg ggtatgggga tcgatcaagt ttgcaaagaa   1320

gatttcgatt ggatcgtaaa tgaacctctc ttggttcgag cttcatcggc aatttgtcga   1380

ttaaccgacg atctagtcgg ggacgagttt gagcaaaaaa cgtcgttggt ggattgttac   1440

atgaaacaac acggtatgtc gaaggacgaa gctcgagctc atcttcgaca acagttgaag   1500

gatgcatgga aggatatgaa ccaagaatcc cttgagccta gaccggcctc gatgccaatc   1560

ctaacgcgtg ttatcaatct cggccgagtc atagatcttc tctattcgga ccatgattgc   1620

tatagtgatc ccaacaaatc gaaaggttgg gtaaagatgg tgctcgtcga ccccatcgca   1680

atttga                                                              1686
```

<210> SEQ ID NO 5
<211> LENGTH: 1816
<212> TYPE: DNA
<213> ORGANISM: Mentha piperita
<220> FEATURE:
<221> NAME/KEY: Gene
<222> LOCATION: (1)..(1816)
<223> OTHER INFORMATION: The partial sequence thus obtained was 759 bp and which was subjected to 3' and 5'RACE in order to get the full-length MPTPS6 gene. Full-length cDNA sequence of MPTPS6 gene was found to be 1821 bp, encoding a polypeptide of 607 amino acids.
<300> PUBLICATION INFORMATION:
<308> DATABASE ACCESSION NUMBER: MH790403
<309> DATABASE ENTRY DATE: 2018-10-24
<313> RELEVANT RESIDUES IN SEQ ID NO: (1)..(1816)

<400> SEQUENCE: 5

```
atgtccacca ttataatggg catgacgctt cccaacaaac ctaccatttg tgttgataac     60

ttcgcaacta aatatccaaa tctgcgccga gcttttccgg tttcatgccg ccgccgtcag    120
```

-continued

```
tcttccgccg tcaaactcag cgctaacact gcttgtacag atgaactcca atctacaaga    180

cgatcgggaa attacgaacc taccctatgg gattttgatc gtattcagtc actcaatagt    240

gtttgcacgg agagggacgg aagaagggca gcggttttga taaaggaagt gaagatgttg    300

ttacaggaag aagtggatgg tgttcttcga cagctggagt tgattgatgc cttgcagagg    360

ctgggtatat cttgtcactt caatgaagaa atcaaacaaa tcttgaattc tttttattac    420

aacgagttca atgatgcaat agttgcagag gaaagggatt tgtacttcac agctcttgca    480

ttcagactac tcagacaaca cggttttaac gtctctcaag aagtctttga ctatttcaag    540

agtgaagagg gtattgatga tttcaagacc atccatgctg aagataccaa agggctgtta    600

caattgtacg aagcatcttt tctatcaaca caaggcgaag aaaccctaga attagcaaga    660

gaatatgccc taaaattttt gcagaaaata ctcgatcatg aaattattaa tgacgaaaat    720

ctctcatcat caattcttcg agatgccata aaaatcccca ttcactggag ggttcaaatg    780

ccaaacgcaa gatcctatat tgatgcctat gagaggaaac ctcgcatgca tccaattgta    840

ctagagctag ccaaactaga gataactatt gttcaagcac gggttcaaca agaactcaaa    900

gagacctcaa ggtggtggca tagcacgagc ctcgttcaac aacttcccct tgtgagggat    960

aggatcgtgg agtgctacta ttggacgacc ggagtccttg agcgtcgaga acatggatat   1020

gagagaataa tgctcaccaa aataaatgct cttgttacaa ctattgatga tatttatgat   1080

atttacggca catttgaaga gctccaacta ttcactaacg cgattaaaag atgggatata   1140

gaatcgatga atcaactacc tccttacatg caacaatgct atcttgcact ccaaaatttt   1200

gttaatgaga tggcttacaa taccctcaag caaaaaggct tcaactcaat cccatatcta   1260

cataaaacgt gggttgattt ggttgaggca tatatgagag aggcagaatg gtaccgcaac   1320

ggtcataaac ctagcctcga agaatatatg aataatgcat ggatatcaat cggaggcgtc   1380

ccgattttat cccatatctt tttctgtgta acagattcta tagatgaagt gaccgttgag   1440

agggtgcatg aataccatga tatagctcgt gcatcatgta cgattcttag gcttgctgat   1500

gatttgggaa catctttgga tgaggtgaag agaggagacg taccgaaatc agttgaatgt   1560

tacatgaatg atgaaaagaa tgcttctgaa caagaggcgc gggcgcatgt acgatctatc   1620

ataaagaata catggaaaac gatgaatgag gaaatgatga cgtcaactaa ttctcaattt   1680

tcaaaatatt ttgtggaagc tgctgctaat cttgggagaa tgtcactttg tatctaccaa   1740

gatgaatgtg atggcttcgg catgcaacat tcaagggtta acaaaatgct aagaggcttg   1800

ctcttcgacc cctgta                                                   1816
```

```
<210> SEQ ID NO 6
<211> LENGTH: 1812
<212> TYPE: DNA
<213> ORGANISM: Mentha piperita
<220> FEATURE:
<221> NAME/KEY: gene
<222> LOCATION: (1)..(1812)
<223> OTHER INFORMATION: The partial sequence thus obtained was 401 bp
      and was subjected to 3' and 5' RACE to get the full-length MPTPS7
      gene. Full-length cDNA sequence of MPTPS7 gene was found to be
      1812 bp, encoding a polypeptide of 604 amino acids.
<300> PUBLICATION INFORMATION:
<308> DATABASE ACCESSION NUMBER: MH790404
<309> DATABASE ENTRY DATE: 2018-10-24
<313> RELEVANT RESIDUES IN SEQ ID NO: (1)..(1812)

<400> SEQUENCE: 6

atgtctaccc ttagcatgca cgtatcgatc tttagcaagc aagttgaaaa taacaacttc     60
```

-continued

```
ttgggcatga gagcttcaaa accaatggcg agacgcgtag cttccactcg cctccgccct    120
atttgctccg ccaccgccac acaaccacaa gttgaagaaa cccgacgttc tggaaactac    180
caggcttcca tttgggactt caattacatt caatctctcc atactccaga ctacaaggaa    240
gagagacttt tgaataggaa agaagagctg atcgtggagg tgaagaagtt gttgaagggg    300
aaaatggagg cagctaagca gttggagctg atcgatgact tgcagaattt gggattgtct    360
tatttttttc aagacgagat taaaaatatc ttgaattgta tatataatga gcacaattat    420
ttccaaaata atattagtaa agtaggggat ttgcatttca ctgctcttgg attcagactc    480
ctcagacagc atggtttcaa cgtttcacaa ggagtatttg agtgtttcaa gaatgaggag    540
ggtagtgatt tcgaggaaac cctaattggg gaagatacga aaggaatatt gcaactttac    600
gaagcatctt tccttttgag agaaggtgaa gatacacttg agctagctag aaaattctca    660
accaaatatc tgcggaaaaa agttgatgag ggaataataa atgatgataa taatctgtta    720
tcatggattc gtcattcttt ggatctccct cttcactgga ggattcaaag actcgaggca    780
agatggttct taaatgctta ctcaaggagg aaagacatga atccacttat tttcgagctc    840
tcaatactcg acttcaatat cattcaagca acacacatac ttgagctcaa agaggtctct    900
aggtggtgga atgaatcggg ccttgttgag aaactaccct ttgtgagaga taggttggtg    960
gaaagctact tttgggccct tggccttttc gaggcccatg attatggata tcagagaaaa   1020
attacaacct taattattgc tctaatcacg gctaccgatg atgtttacga tgtttatggt   1080
acattagacg aactccgctt atttacagat gcgattcgaa gatgggatac aaaatcaata   1140
gaccaacttc cgtattacat gcaactctgc tatttggcac tccacaactt agtttccgag   1200
atggcttacg attgtctcaa acataaacag ttcaacagta ttccatattt tcagcgatcg   1260
tgggtgagtt tgggggaagg atatttgaaa gaggcagagt ggttcgaaag tggatacaca   1320
ccaaccctag atgaatacct caacaacgcc aagatttcaa taggctctcc cacaataatc   1380
acccaagttt acttaacctt actaaactcg agcaccgacc aacaagtcct tgatagcttg   1440
tacgagtacc acaacatact ctatctttcc ggtatagttt taaggcttgc tgacgatcta   1500
ggtacatcac agtttgagct gaagagaggg gacgtaccaa aagcgttgca gtgctgcatg   1560
aaggacatga aatgtaggga gaaagaggcg gaagaacacc tgcggtttct gatccgagag   1620
gcgtggaagg agattaacac aacgatgggg gcggaagctg cagattgtcc gtacaaagat   1680
gatttgtttg aggctgcggc taaccttgga agagctgctc agtttatata tttggaggga   1740
gatggtcatg gcgttcagca ttccggaata catcaccaga tggccagctc aatgttccac   1800
ccatatatat ga                                                       1812
```

<210> SEQ ID NO 7
<211> LENGTH: 797
<212> TYPE: DNA
<213> ORGANISM: Mentha piperita
<220> FEATURE:
<221> NAME/KEY: promoter
<222> LOCATION: (1)..(797)

<400> SEQUENCE: 7

```
aaaaaatggg tacttttatt cggtaaaatt aattatatta aagatggaca cttcattggc     60
tgtggcatcg agcgcgagct ccatgccgtg tgagcggcac gaccacgact gcctccctca    120
tgttttgccc atgcatcgtg tgttggcacg tcggggcttc ccgtcggtcg tgcaacgggt    180
gcgagcctcc gtcgggagag gtgtctggcg ggccgtacga ttgcacaacc aagactaccc    240
```

-continued

```
tcgagtcgtg gtcgtgcaat gccacgtcgg gcgccgtgtt cactgtgccg tgcgaaatac    300

aagaccaata ttacacgaca atgtagttgt gtaatcgtgg tcatgtaatt aacttaagag    360

gttaatttat cattttacac gaaaaaataa ctaaaatttg catattgttt tatatgtggc    420

taaaatttag ctttacatta tcaaaatgac tattttgggg attgccctct atatatattg    480

tttctaatag tacattttaa gtgatttcag ataataaata aatacagcca aacaaattaa    540

acaacaacgg ctatatagcg ttgataaatg caccttctag ctagaatgac ttatatagta    600

gcataatacg aaatccaaaa gaaggttgaa gttgtgatgt atttcattaa ttaggccgaa    660

aaaatagaaa cgtgcatgct taatctatag gagtctgtat aaatagaaat atgcatctca    720

aattttagaa accagtacgt cctagaaaaa catagaaaga gagtggaaga aaaggagaaa    780

gcaaagatta attaatc                                                   797


<210> SEQ ID NO 8
<211> LENGTH: 3514
<212> TYPE: DNA
<213> ORGANISM: Mentha piperita
<220> FEATURE:
<221> NAME/KEY: modified_base
<222> LOCATION: (1)..(3514)
<223> OTHER INFORMATION: The MPTPS4 (1686 bp) gene was cloned in
      pHANNIBALvector system by replacing the PDK intron to yield
      phannibal-MPTPS4,under tissue specific promoter (Limonene
      synthase, 797 bp).

<400> SEQUENCE: 8

ggccgctcga cgaattaatt ccaatcccac aaaaatctga gcttaacagc acagttgctc     60

ctctcagagc agaatcgggt attcaacacc ctcatatcaa ctactacgtt gtgtataacg    120

gtccacatgc cggtatatac gatgactggg gttgtacaaa ggcggcaaca aacggcgttc    180

ccggagttgc acacaagaaa tttgccacta ttacagaggc aagagcagca gctgacgcgt    240

aaaaaatggg tacttttatt cggtaaaatt aattatatta aagatggaca cttcattggc    300

tgtggcatcg agcgcgagct ccatgccgtg tgagcggcac gaccacgact gcctccctca    360

tgttttgccc atgcatcgtg tgttggcacg tcggggcttc ccgtcggtcg tgcaacgggt    420

gcgagcctcc gtcgggagag gtgtctggcg ggccgtacga ttgcacaacc aagactaccc    480

tcgagtcgtg gtcgtgcaat gccacgtcgg gcgccgtgtt cactgtgccg tgcgaaatac    540

aagaccaata ttacacgaca atgtagttgt gtaatcgtgg tcatgtaatt aacttaagag    600

gttaatttat cattttacac gaaaaaataa ctaaaatttg catattgttt tatatgtggc    660

taaaatttag ctttacatta tcaaaatgac tattttgggg attgccctct atatatattg    720

tttctaatag tacattttaa gtgatttcag ataataaata aatacagcca aacaaattaa    780

acaacaacgg ctatatagcg ttgataaatg caccttctag ctagaatgac ttatatagta    840

gcataatacg aaatccaaaa gaaggttgaa gttgtgatgt atttcattaa ttaggccgaa    900

aaaatagaaa cgtgcatgct taatctatag gagtctgtat aaatagaaat atgcatctca    960

aattttagaa accagtacgt cctagaaaaa catagaaaga gagtggaaga aaaggagaaa   1020

gcaaagatta attaatcgaa ttcatggaaa tttattcccc agttgttcct gcaatcaaag   1080

atgtgaagag gttggatgaa atccgaaaat ccgccaaata ccatccaact atttggggag   1140

actttttct agcgtataat tccgataata cgaaaatctc tgatggtgaa gaagaagaag   1200

ttgcaaagca gaaagaaatg gtacggaaac tgctagctga agccccagaa aattccacct   1260

acaaaatgga actcatcgat acaatccagc gcctgggagt ggaatatcat tttgaaaaag   1320
```

aaatcgaaat atccttgaaa tatattcatg agaattatgt gcaccaaaac agcaaagacg 1380
acgatcttca caccgtggct cttcgttttc gtttgcttag acaacaaggt tacaacgtcc 1440
catgcgacgt tttcagcaaa ttcaccgacc gtgaaggaaa ttttgcggcg gcgctgagaa 1500
atgacgttga aagtttgttg gaattatatg aggcgtcgca tctcgcgaca cgtggcgagg 1560
aaattctgga cagcgcaatg gagttgtgtt cttcccatct ccaagcatta gtaaatgatc 1620
agcagttggt gaacaatgtt tctctctcta aacgagtgat tgaagctctg aagatgccaa 1680
ttcgcaagag tctcacgaga ttgggtgcga gaaagttcat ctctctatac caagaggatg 1740
attcgcataa tgaaatactt ttgaattttg cgaaattaga tttcaatata gtgcagaaga 1800
tgcaccagag agagcttagt gatgctacga ggtggtggaa gaagttggac gtggcgaata 1860
aaatgcctta cgcaagagac agaaatgtgg agtgcttctt tttggatggt gggcgtctac 1920
ttcgagcatg ctacgctact gcaagaaaaa tattacttaa atgcataagt atggcttcaa 1980
ttattgatga cacctacgaa tatgcaaccc tacatgaact gcaaattctc accgacgcta 2040
tccaacgttg ggatgttaat gaggcattgg aggattcgcc accatatata caaatgtgct 2100
acagaagcct tattcaaact tatgttgaaa tagaagatga agtagtggag aaatttggag 2160
gagaatcgtc ataccgtgtc caatatgcaa tacaagatat gaaaaaatcg gtgtgggcat 2220
atatggaaga ggcgaaatgg atgtatgacg attatattcc aaccgtggag gagtatatga 2280
aggtttcgat cgtatcttgt ggttatatga caatgtcaac cacttcttta gtgggtatgg 2340
ggatcgatca agtttgcaaa gaagatttcg attggatcgt aaatgaacct ctcttggttc 2400
gagcttcatc ggcaatttgt cgattaaccg acgatctagt cggggacgag tttgagcaaa 2460
aaacgtcgtt ggtggattgt tacatgaaac aacacggtat gtcgaaggac gaagctcgag 2520
ctcatcttcg acaacagttg aaggatgcat ggaaggatat gaaccaagaa tcccttgagc 2580
ctagaccggc ctcgatgcca atcctaacgc gtgttatcaa tctcggccga gtcatagatc 2640
ttctctattc ggaccatgat tgctatagtg atcccaacaa atcgaaaggt tgggtaaaga 2700
tggtgctcgt cgaccccatc gcaatttgag gatcctctag agtcctgctt taatgagata 2760
tgcgagacgc ctatgatcgc atgatatttg ctttcaattc tgttgtgcac gttgtaaaaa 2820
acctgagcat gtgtagctca gatccttacc gccggtttcg gttcattcta atgaatatat 2880
cacccgttac tatcgtattt ttatgaataa tattctccgt tcaatttact gattgtaccc 2940
tactacttat atgtacaata ttaaaatgaa aacaatatat tgtgctgaat aggtttatag 3000
cgacatctat gatagagcgc cacaataaca aacaattgcg ttttattatt acaaatccaa 3060
ttttaaaaaa agcggcagaa ccggtcaaac ctaaaagact gattacataa atcttattca 3120
aatttcaaaa ggccccaggg gctagtatct acgacacacc gagcggcgaa ctaataacgt 3180
tcactgaagg gaactccggt tccccgccgg cgcgcatggg tgagattcct tgaagttgag 3240
tattggccgt ccgctctacc gaaagttacg ggcaccattc aacccggtcc agcacggcgg 3300
ccgggtaacc gacttgctgc cccgagaatt atgcagcatt tttttggtgt atgtgggccc 3360
caaatgaagt gcaggtcaaa ccttgacagt gacgacaaat cgttgggcgg gtccagggcg 3420
aattttgcga caacatgtcg aggctcagca ggacctgcag gcatgcaagc tagcttacta 3480
gtgatgcata ttctatagtg tcacctaaat ctgc 3514

<210> SEQ ID NO 9
<211> LENGTH: 15181
<212> TYPE: DNA

```
<213> ORGANISM: Mentha piperita
<220> FEATURE:
<221> NAME/KEY: modified_base
<222> LOCATION: (1)..(15181)
<223> OTHER INFORMATION: The whole cassette of SEQUENCE ID NO.8 was
      cloned into pART27 binary vector system.

<400> SEQUENCE: 9

tcgacatctt gctgcgttcg gatattttcg tggagttccc gccacagacc cggattgaag     60

gcgagatcca gcaactcgcg ccagatcatc ctgtgacgga actttggcgc gtgatgactg    120

gccaggacgt cggccgaaag agcgacaagc agatcacgat tttcgacagc gtcggatttg    180

cgatcgagga tttttcggcg ctgcgctacg tccgcgaccg cgttgaggga tcaagccaca    240

gcagcccact cgaccttcta gccgacccag acgagccaag ggatcttttt ggaatgctgc    300

tccgtcgtca ggctttccga cgtttgggtg gttgaacaga agtcattatc gtacggaatg    360

ccagcactcc cgaggggaac cctgtggttg gcatgcacat acaaatggac gaacggataa    420

accttttcac gcccttttaa atatccgtta ttctaataaa cgctcttttc tcttaggttt    480

acccgccaat atatcctgtc aaacactgat agtttaaact gaaggcggga aacgacaatc    540

tgatcatgag cggagaatta agggagtcac gttatgaccc ccgccgatga cgcgggacaa    600

gccgttttac gtttggaact gacagaaccg caacgattga aggagccact cagccccaat    660

acgcaaaccg cctctccccg cgcgttggcc gattcattaa tgcagctggc acgacaggtt    720

tcccgactgg aaagcgggca gtgagcgcaa cgcaattaat gtgagttagc tcactcatta    780

ggcaccccag gctttacact ttatgcttcc ggctcgtatg ttgtgtggaa ttgtgagcgg    840

ataacaattt cacacaggaa acagctatga ccatgattac gccaagctat ttaggtgaca    900

ctatagaata ctcaagctat gcatccaacg cgttgggagc tctcccatat cgacctgcag    960

gcggccgctc gacgaattaa ttccaatccc acaaaaatct gagcttaaca gcacagttgc   1020

tcctctcaga gcagaatcgg gtattcaaca ccctcatatc aactactacg ttgtgtataa   1080

cggtccacat gccggtatat acgatgactg gggttgtaca aaggcggcaa caaacggcgt   1140

tcccggagtt gcacacaaga aatttgccac tattacagag gcaagagcag cagctgacgc   1200

gtaaaaaatg ggtactttta ttcggtaaaa ttaattatat taaagatgga cacttcattg   1260

gctgtggcat cgagcgcgag ctccatgccg tgtgagcggc acgaccacga ctgcctccct   1320

catgttttgc ccatgcatcg tgtgttggca cgtcggggct tcccgtcggt cgtgcaacgg   1380

gtgcgagcct ccgtcgggag aggtgtctgg cgggccgtac gattgcacaa ccaagactac   1440

cctcgagtcg tggtcgtgca atgccacgtc gggcgccgtg ttcactgtgc cgtgcgaaat   1500

acaagaccaa tattacacga caatgtagtt gtgtaatcgt ggtcatgtaa ttaacttaag   1560

aggttaattt atcattttac acgaaaaaat aactaaaatt tgcatattgt tttatatgtg   1620

gctaaaattt agctttacat tatcaaaatg actattttgg ggattgccct ctatatatat   1680

tgtttctaat agtacatttt aagtgatttc agataataaa taaatacagc caaacaaatt   1740

aaacaacaac ggctatatag cgttgataaa tgcaccttct agctagaatg acttatatag   1800

tagcataata cgaaatccaa aagaaggttg aagttgtgat gtatttcatt aattaggccg   1860

aaaaaataga aacgtgcatg cttaatctat aggagtctgt ataaatagaa atatgcatct   1920

caaattttag aaaccagtac gtcctagaaa aacatagaaa gagagtggaa gaaaaggaga   1980

aagcaaagat taattaatcg aattcatgga aatttattcc ccagttgttc ctgcaatcaa   2040

agatgtgaag aggttggatg aaatccgaaa atccgccaaa taccatccaa ctatttgggg   2100
```

-continued

```
agactttttt ctagcgtata attccgataa tacgaaaatc tctgatggtg aagaagaaga   2160
agttgcaaag cagaaagaaa tggtacggaa actgctagct gaagccccag aaaattccac   2220
ctacaaaatg gaactcatcg atacaatcca gcgcctggga gtggaatatc attttgaaaa   2280
agaaatcgaa atatccttga aatatattca tgagaattat gtgcaccaaa acagcaaaga   2340
cgacgatctt cacaccgtgg ctcttcgttt tcgtttgctt agacaacaag gttacaacgt   2400
cccatgcgac gttttcagca aattcaccga ccgtgaagga aattttgcgg cggcgctgag   2460
aaatgacgtt gaaagtttgt tggaattata tgaggcgtcg catctcgcga cacgtggcga   2520
ggaaattctg gacagcgcaa tggagttgtg ttcttcccat ctccaagcat tagtaaatga   2580
tcagcagttg gtgaacaatg tttctctctc taaacgagtg attgaagctc tgaagatgcc   2640
aattcgcaag agtctcacga gattgggtgc gagaaagttc atctctctat accaagagga   2700
tgattcgcat aatgaaatac ttttgaattt tgcgaaatta gatttcaata tagtgcagaa   2760
gatgcaccag agagagctta gtgatgctac gaggtggtgg aagaagttgg acgtggcgaa   2820
taaaatgcct tacgcaagag acagaaatgt ggagtgcttc tttttggatg gtgggcgtct   2880
acttcgagca tgctacgcta ctgcaagaaa aatattactt aaatgcataa gtatggcttc   2940
aattattgat gacacctacg aatatgcaac cctacatgaa ctgcaaattc tcaccgacgc   3000
tatccaacgt tgggatgtta atgaggcatt ggaggattcg ccaccatata tacaaatgtg   3060
ctacagaagc cttattcaaa cttatgttga aatagaagat gaagtagtgg agaaatttgg   3120
aggagaatcg tcataccgtg tccaatatgc aatacaagat atgaaaaaat cggtgtgggc   3180
atatatggaa gaggcgaaat ggatgtatga cgattatatt ccaaccgtgg aggagtatat   3240
gaaggtttcg atcgtatctt gtggttatat gacaatgtca accacttctt tagtgggtat   3300
ggggatcgat caagtttgca aagaagattt cgattggatc gtaaatgaac ctctcttggt   3360
tcgagcttca tcggcaattt gtcgattaac cgacgatcta gtcggggacg agtttgagca   3420
aaaaacgtcg ttggtggatt gttacatgaa acaacacggt atgtcgaagg acgaagctcg   3480
agctcatctt cgacaacagt tgaaggatgc atggaaggat atgaaccaag aatcccttga   3540
gcctagaccg gcctcgatgc caatcctaac gcgtgttatc aatctcggcc gagtcataga   3600
tcttctctat tcggaccatg attgctatag tgatcccaac aaatcgaaag gttgggtaaa   3660
gatggtgctc gtcgaccccca tcgcaatttg aggatcctct agagtcctgc tttaatgaga   3720
tatgcgagac gcctatgatc gcatgatatt tgctttcaat tctgttgtgc acgttgtaaa   3780
aaacctgagc atgtgtagct cagatcctta ccgccggttt cggttcattc taatgaatat   3840
atcacccgtt actatcgtat ttttatgaat aatattctcc gttcaattta ctgattgtac   3900
cctactactt atatgtacaa tattaaaatg aaaacaatat attgtgctga ataggtttat   3960
agcgacatct atgatagagc gccacaataa caaacaattg cgttttatta ttacaaatcc   4020
aattttaaaa aaagcggcag aaccggtcaa acctaaaaga ctgattacat aaatcttatt   4080
caaatttcaa aaggccccag gggctagtat ctacgacaca ccgagcggcg aactaataac   4140
gttcactgaa gggaactccg gttccccgcc ggcgcgcatg ggtgagattc cttgaagttg   4200
agtattggcc gtccgctcta ccgaaagtta cgggcaccat tcaacccggt ccagcacggc   4260
ggccgggtaa ccgacttgct gccccgagaa ttatgcagca ttttttggt gtatgtgggc   4320
cccaaatgaa gtgcaggtca aaccttgaca gtgacgacaa atcgttgggc gggtccaggg   4380
cgaattttgc gacaacatgt cgaggctcag caggacctgc aggcatgcaa gctagcttac   4440
tagtgatgca tattctatag tgtcacctaa atctgcggcc gcactagtga tatcccgcgg   4500
```

-continued

```
ccatggcggc cgggagcatg cgacgtcggg cccaattcgc cctatagtga gtcgtattac   4560
aattcactgg ccgtcgtttt acaacgtcgt gactgggaaa accctggcgt tacccaactt   4620
aatcgccttg cagcacatcc ccctttcgcc agctggcgta atagcgaaga ggcccgcacc   4680
gatcgccctt cccaacagtt gcgcagcctg aatggcgaat ggaaattgta aacgttaatg   4740
ggtttctgga gtttaatgag ctaagcacat acgtcagaaa ccattattgc gcgttcaaaa   4800
gtcgcctaag gtcactatca gctagcaaat atttcttgtc aaaaatgctc cactgacgtt   4860
ccataaattc ccctcggtat ccaattagag tctcatattc actctcaatc caaataatct   4920
gcaatggcaa ttaccttatc cgcaacttct ttacctattt ccgcccggat ccgggcaggt   4980
tctccggccg cttgggtgga gaggctattc ggctatgact gggcacaaca gacaatcggc   5040
tgctctgatg ccgccgtgtt ccggctgtca gcgcaggggc gcccggttct ttttgtcaag   5100
accgacctgt ccggtgccct gaatgaactg caggacgagg cagcgcggct atcgtggctg   5160
gccacgacgg gcgttccttg cgcagctgtg ctcgacgttg tcactgaagc gggaagggac   5220
tggctgctat tgggcgaagt gccggggcag gatctcctgt catctcacct tgctcctgcc   5280
gagaaagtat ccatcatggc tgatgcaatg cggcggctgc atacgcttga tccggctacc   5340
tgcccattcg accaccaagc gaaacatcgc atcgagcgag cacgtactcg gatggaagcc   5400
ggtcttgtcg atcaggatga tctggacgaa gagcatcagg ggctcgcgcc agccgaactg   5460
ttcgccaggc tcaaggcgcg catgcccgac ggcgaggatc tcgtcgtgac ccatggcgat   5520
gcctgcttgc cgaatatcat ggtggaaaat ggccgctttt ctggattcat cgactgtggc   5580
cggctgggtg tggcggaccg ctatcaggac atagcgttgg ctacccgtga tattgctgaa   5640
gagcttggcg gcgaatgggc tgaccgcttc ctcgtgcttt acggtatcgc cgctcccgat   5700
tcgcagcgca tcgccttcta tcgccttctt gacgagttct tctgagcggg actctggggt   5760
tcgaaatgac cgaccaagcg acgcccaacc tgccatcacg agatttcgat tccaccgccg   5820
ccttctatga aaggttgggc ttcggaatcg ttttccggga cgccggctgg atgatcctcc   5880
agcgcgggga tctcatgctg gagttcttcg cccaccccga tccaacactt acgtttgcaa   5940
cgtccaagag caaatagacc acgaacgccg gaaggttgcc gcagcgtgtg gattgcgtct   6000
caattctctc ttgcaggaat gcaatgatga atatgatact gactatgaaa ctttgaggga   6060
atactgccta gcaccgtcac ctcataacgt gcatcatgca tgccctgaca acatggaaca   6120
tcgctatttt tctgaagaat tatgctcgtt ggaggatgtc gcggcaattg cagctattgc   6180
caacatcgaa ctacccctca cgcatgcatt catcaatatt attcatgcgg ggaaaggcaa   6240
gattaatcca actggcaaat catccagcgt gattggtaac ttcagttcca gcgacttgat   6300
tcgttttggt gctacccacg ttttcaataa ggacgagatg gtggagtaaa gaaggagtgc   6360
gtcgaagcag atcgttcaaa catttggcaa taaagtttct taagattgaa tcctgttgcc   6420
ggtcttgcga tgattatcat ataatttctg ttgaattacg ttaagcatgt aataattaac   6480
atgtaatgca tgacgttatt tatgagatgg gtttttatga ttagagtccc gcaattatac   6540
atttaatacg cgatagaaaa caaaatatag cgcgcaaact aggataaatt atcgcgcgcg   6600
gtgtcatcta tgttactaga tcgaattaat tccaggcggt gaagggcaat cagctgttgc   6660
ccgtctcact ggtgaaaaga aaaaccaccc cagtacatta aaaacgtccg caatgtgtta   6720
ttaagttgtc taagcgtcaa tttgtttaca ccacaatata tcctgccacc agccagccaa   6780
cagctccccg accggcagct cggcacaaaa tcaccactcg atacaggcag cccatcagtc   6840
```

-continued

```
cgggacggcg tcagcgggag agccgttgta aggcggcaga ctttgctcat gttaccgatg   6900
ctattcggaa gaacggcaac taagctgccg ggtttgaaac acggatgatc tcgcggaggg   6960
tagcatgttg attgtaacga tgacagagcg ttgctgcctg tgatcaaata tcatctccct   7020
cgcagagatc cgaattatca gccttcttat tcatttctcg cttaaccgtg acaggctgtc   7080
gatcttgaga actatgccga cataatagga aatcgctgga taaagccgct gaggaagctg   7140
agtggcgcta tttctttaga agtgaacgtt gacgatgtcg acggatcttt tccgctgcat   7200
aaccctgctt cggggtcatt atagcgattt tttcggtata tccatccttt ttcgcacgat   7260
atacaggatt ttgccaaagg gttcgtgtag actttccttg gtgtatccaa cggcgtcagc   7320
cgggcaggat aggtgaagta ggcccacccg cgagcgggtg ttccttcttc actgtccctt   7380
attcgcacct ggcggtgctc aacgggaatc ctgctctgcg aggctggccg gctaccgccg   7440
gcgtaacaga tgagggcaag cggatggctg atgaaaccaa gccaaccagg ggtgatgctg   7500
ccaacttact gatttagtgt atgatggtgt ttttgaggtg ctccagtggc ttctgtttct   7560
atcagctgtc cctcctgttc agctactgac ggggtggtgc gtaacggcaa aagcaccgcc   7620
ggacatcagc gctatctctg ctctcactgc cgtaaaacat ggcaactgca gttcacttac   7680
accgcttctc aacccggtac gcaccagaaa atcattgata tggccatgaa tggcgttgga   7740
tgccgggcaa cagcccgcat tatgggcgtt ggcctcaaca cgattttacg tcacttaaaa   7800
aactcaggcc gcagtcggta acctcgcgca tacagccggg cagtgacgtc atcgtctgcg   7860
cggaaatgga cgaacagtgg ggctatgtcg ggggctaaatc gcgccagcgc tggctgtttt   7920
acgcgtatga cagtctccgg aagacggttg ttgcgcacgt attcggtgaa cgcactatgg   7980
cgacgctggg gcgtcttatg agcctgctgt caccctttga cgtggtgata tggatgacgg   8040
atggctggcc gctgtatgaa tcccgcctga agggaaagct gcacgtaatc agcaagcgat   8100
atacgcagcg aattgagcgg cataacctga atctgaggca gcacctggca cggctgggac   8160
ggaagtcgct gtcgttctca aaatcggtgg agctgcatga caaagtcatc gggcattatc   8220
tgaacataaa acactatcaa taagttggag tcattaccca accaggaagg gcagcccacc   8280
tatcaaggtg tactgccttc cagacgaacg aagagcgatt gaggaaaagg cggcggcggc   8340
cggcatgagc ctgtcggcct acctgctggc cgtcggccag ggctacaaaa tcacgggcgt   8400
cgtggactat gagcacgtcc gcgagctggc ccgcatcaat ggcgacctgg gccgcctggg   8460
cggcctgctg aaactctggc tcaccgacga cccgcgcacg gcgcggttcg gtgatgccac   8520
gatcctcgcc ctgctggcga agatcgaaga gaagcaggac gagcttggca aggtcatgat   8580
gggcgtggtc cgcccgaggg cagagccatg actttttag ccgctaaaac ggccgggggg   8640
tgcgcgtgat tgccaagcac gtccccatgc gctccatcaa gaagagcgac ttcgcggagc   8700
tggtattcgt gcagggcaag attcggaata ccaagtacga gaaggacggc cagacggtct   8760
acgggaccga cttcattgcc gataaggtgg attatctgga caccaaggca ccaggcgggt   8820
caaatcagga ataagggcac attgccccgg cgtgagtcgg ggcaatcccg caaggagggt   8880
gaatgaatcg gacgtttgac cggaaggcat acaggcaaga actgatcgac gcggggtttt   8940
ccgccgagga tgccgaaacc atcgcaagcc gcaccgtcat gcgtgcgccc cgcgaaacct   9000
tccagtccgt cggctcgatg gtccagcaag ctacggccaa gatcgagcgc gacagcgtgc   9060
aactggctcc ccctgccctg cccgcgccat cggccgccgt ggagcgttcg cgtcgtctcg   9120
aacaggaggc ggcaggtttg gcgaagtcga tgaccatcga cacgcgagga actatgacga   9180
ccaagaagcg aaaaaccgcc ggcgaggacc tggcaaaaca ggtcagcgag gccaagcagg   9240
```

-continued

```
ccgcgttgct gaaacacacg aagcagcaga tcaaggaaat gcagctttcc ttgttcgata   9300
ttgcgccgtg gccggacacg atgcgagcga tgccaaacga cacggcccgc tctgccctgt   9360
tcaccacgcg caacaagaaa atcccgcgcg aggcgctgca aaacaaggtc attttccacg   9420
tcaacaagga cgtgaagatc acctacaccg gcgtcgagct gcgggccgac gatgacgaac   9480
tggtgtggca gcaggtgttg gagtacgcga agcgcacccc tatcggcgag ccgatcacct   9540
tcacgttcta cgagctttgc caggacctgg gctggtcgat caatggccgg tattacacga   9600
aggccgagga atgcctgtcg cgcctacagg cgacggcgat gggcttcacg tccgaccgcg   9660
ttgggcacct ggaatcggtg tcgctgctgc accgcttccg cgtcctggac cgtggcaaga   9720
aaacgtcccg ttgccaggtc ctgatcgacg aggaaatcgt cgtgctgttt gctggcgacc   9780
actacacgaa attcatatgg gagaagtacc gcaagctgtc gccgacggcc cgacggatgt   9840
tcgactattt cagctcgcac cgggagccgt acccgctcaa gctggaaacc ttccgcctca   9900
tgtgcggatc ggattccacc cgcgtgaaga agtggcgcga gcaggtcggc gaagcctgcg   9960
aagagttgcg aggcagcggc ctggtggaac acgcctgggt caatgatgac ctggtgcatt  10020
gcaaacgcta gggccttgtg gggtcagttc cggctggggg ttcagcagcc agcgctttac  10080
tggcatttca ggaacaagcg ggcactgctc gacgcacttg cttcgctcag tatcgctcgg  10140
gacgcacggc gcgctctacg aactgccgat aaacagagga ttaaaattga caattgtgat  10200
taaggctcag attcgacggc ttggagcggc cgacgtgcag gatttccgcg agatccgatt  10260
gtcggccctg aagaaagctc cagagatgtt cgggtccgtt tacgagcacg aggagaaaaa  10320
gcccatggag gcgttcgctg aacggttgcg agatgccgtg gcattcggcg cctacatcga  10380
cggcgagatc attgggctgt cggtcttcaa acaggaggac ggccccaagg acgctcacaa  10440
ggcgcatctg tccggcgttt tcgtggagcc cgaacagcga ggccgagggg tcgccggtat  10500
gctgctgcgg gcgttgccgg cgggtttatt gctcgtgatg atcgtccgac agattccaac  10560
gggaatctgg tggatgcgca tcttcatcct cggcgcactt aatatttcgc tattctggag  10620
cttgttgttt atttcggtct accgcctgcc gggcggggtc gcggcgacgg taggcgctgt  10680
gcagccgctg atggtcgtgt tcatctctgc cgctctgcta ggtagcccga tacgattgat  10740
ggcggtcctg ggggctattt gcggaactgc gggcgtggcg ctgttggtgt tgacaccaaa  10800
cgcagcgcta gatcctgtcg gcgtcgcagc gggcctggcg ggggcggttt ccatggcgtt  10860
cggaaccgtg ctgacccgca agtggcaacc tcccgtgcct ctgctcacct ttaccgcctg  10920
gcaactggcg gccggaggac ttctgctcgt tccagtagct ttagtgtttg atccgccaat  10980
cccgatgcct acaggaacca atgttctcgg cctggcgtgg ctcggcctga tcggagcggg  11040
tttaacctac ttcctttggt tccgggggat ctcgcgactc gaacctacag ttgtttcctt  11100
actgggcttt ctcagccggg atggcgctaa gaagctattg ccgccgatct tcatatgcgg  11160
tgtgaaatac cgcacagatg cgtaaggaga aaataccgca tcaggcgctc ttccgcttcc  11220
tcgctcactg actcgctgcg ctcggtcgtt cggctgcggc gagcggtatc agctcactca  11280
aaggcggtaa tacggttatc cacagaatca ggggataacg caggaaagaa catgtgagca  11340
aaaggccagc aaaaggccag gaaccgtaaa aaggccgcgt tgctggcgtt tttccatagg  11400
ctccgccccc ctgacgagca tcacaaaaat cgacgctcaa gtcagaggtg gcgaaacccg  11460
acaggactat aaagatacca ggcgtttccc cctggaagct ccctcgtgcg ctctcctgtt  11520
ccgaccctgc cgcttaccgg atacctgtcc gcctttctcc cttcgggaag cgtggcgctt  11580
```

-continued

```
tctcaatgct cacgctgtag gtatctcagt tcggtgtagg tcgttcgctc caagctgggc  11640
tgtgtgcacg aaccccccgt tcagcccgac cgctgcgcct tatccggtaa ctatcgtctt  11700
gagtccaacc cggtaagaca cgacttatcg ccactggcag cagccactgg taacaggatt  11760
agcagagcga ggtatgtagg cggtgctaca gagttcttga agtggtggcc taactacggc  11820
tacactagaa ggacagtatt tggtatctgc gctctgctga agccagttac cttcggaaaa  11880
agagttggta gctcttgatc cggcaaacaa accaccgctg gtagcggtgg tttttttgtt  11940
tgcaagcagc agattacgcg cagaaaaaaa ggatatcaag aagatccttt gatcttttct  12000
acggggtctg acgctcagtg gaacgaaaac tcacgttaag ggattttggt catgagatta  12060
tcaaaaagga tcttcaccta gatcctttta aattaaaaat gaagttttaa atcaatctaa  12120
agtatatatg agtaaacttg gtctgacagt taccaatgct taatcagtga ggcacctatc  12180
tcagcgatct gtctatttcg ttcatccata gttgcctgac tccccgtcgt gtagataact  12240
acgatacggg agggcttacc atctggcccc agtgctgcaa tgataccgcg agacccacgc  12300
tcaccggctc cagatttatc agcaataaac cagccagccg gaagggccga gcgcagaagt  12360
ggtcctgcaa ctttatccgc ctccatccag tctattaaac aagtggcagc aacggattcg  12420
caaacctgtc acgccttttg tgccaaaagc cgcgccaggt ttgcgatccg ctgtgccagg  12480
cgttaggcgt catatgaaga tttcggtgat ccctgagcag gtggcggaaa cattggatgc  12540
tgagaaccat ttcattgttc gtgaagtgtt cgatgtgcac ctatccgacc aaggctttga  12600
actatctacc agaagtgtga gcccctaccg gaaggattac atctcggatg atgactctga  12660
tgaagactct gcttgctatg gcgcattcat cgaccaagag cttgtcggga agattgaact  12720
caactcaaca tggaacgatc tagcctctat cgaacacatt gttgtgtcgc acacgcaccg  12780
aggcaaagga gtcgcgcaca gtctcatcga atttgcgaaa aagtgggcac taagcagaca  12840
gctccttggc atacgattag agacacaaac gaacaatgta cctgcctgca atttgtacgc  12900
aaaatgtggc tttactctcg gcggcattga cctgttcacg tataaaacta gacctcaagt  12960
ctcgaacgaa acagcgatgt actggtactg gttctcggga gcacaggatg acgcctaaca  13020
attcattcaa gccgacaccg cttcgcggcg cggcttaatt caggagttaa acatcatgag  13080
ggaagcggtg atcgccgaag tatcgactca actatcagag gtagttggcg tcatcgagcg  13140
ccatctcgaa ccgacgttgc tggccgtaca tttgtacggc tccgcagtgg atggcggcct  13200
gaagccacac agtgatattg atttgctggt tacggtgacc gtaaggcttg atgaaacaac  13260
gcggcgagct ttgatcaacg accttttgga aacttcggct tcccctggag agagcgagat  13320
tctccgcgct gtagaagtca ccattgttgt gcacgacgac atcattccgt ggcgttatcc  13380
agctaagcgc gaactgcaat ttggagaatg gcagcgcaat gacattcttg caggtatctt  13440
cgagccagcc acgatcgaca ttgatctggc tatcttgctg acaaaagcaa gagaacatag  13500
cgttgccttg gtaggtccag cggcggagga actctttgat ccggttcctg aacaggatct  13560
atttgaggcg ctaaatgaaa ccttaacgct atggaactcg ccgcccgact gggctggcga  13620
tgagcgaaat gtagtgctta cgttgtcccg catttggtac agcgcagtaa ccggcaaaat  13680
cgcgccgaag gatgtcgctg ccgactgggc aatggagcgc ctgccggccc agtatcagcc  13740
cgtcatactt gaagctaggc aggcttatct tggacaagaa gatcgcttgg cctcgcgcgc  13800
agatcagttg gaagaatttg ttcactacgt gaaaggcgag atcaccaagg tagtcggcaa  13860
ataatgtcta acaattcgtt caagccgacg ccgcttcgcg gcgcggctta actcaagcgt  13920
tagagagctg ggaagacta tgcgcgatct gttgaaggtg gttctaagcc tcgtacttgc  13980
```

```
gatggcatcg gggcaggcac ttgctgacct gccaattgtt ttagtggatg aagctcgtct  14040

tccctatgac tactccccat ccaactacga catttctcca agcaactacg acaactccat  14100

aagcaattac gacaatagtc catcaaatta cgacaactct gagagcaact acgataatag  14160

ttcatccaat tacgacaata gtcgcaacgg aaatcgtagg cttatatata gcgcaaatgg  14220

gtctcgcact ttcgccggct actacgtcat tgccaacaat gggacaacga acttcttttc  14280

cacatctggc aaaaggatgt tctacacccc aaaagggggg cgcggcgtct atggcggcaa  14340

agatgggagc ttctgcgggg cattggtcgt cataaatggc caattttcgc ttgccctgac  14400

agataacggc ctgaagatca tgtatctaag caactagcct gctctctaat aaaatgttag  14460

gagcttggct gccatttttg gggtgaggcc gttcgcggcc gaggggcgca gcccctgggg  14520

ggatgggagg cccgcgttag cgggccggga gggttcgaga aggggggggca cccccccttcg  14580

gcgtgcgcgg tcacgcgcca gggcgcagcc ctggttaaaa acaaggttta taaatattgg  14640

tttaaaagca ggttaaaaga caggttagcg gtggccgaaa aacgggcgga aacccttgca  14700

aatgctggat tttctgcctg tggacagccc ctcaaatgtc aataggtgcg cccctcatct  14760

gtcagcactc tgcccctcaa gtgtcaagga tcgcgcccct catctgtcag tagtcgcgcc  14820

cctcaagtgt caataccgca gggcacttat ccccaggctt gtccacatca tctgtgggaa  14880

actcgcgtaa aatcaggcgt tttcgccgat ttgcgaggct ggccagctcc acgtcgccgg  14940

ccgaaatcga gcctgcccct catctgtcaa cgccgcgccg ggtgagtcgg cccctcaagt  15000

gtcaacgtcc gcccctcatc tgtcagtgag ggccaagttt tccgcgaggt atccacaacg  15060

ccggcggccg gccgcggtgt ctcgcacacg gcttcgacgg cgtttctggc gcgtttgcag  15120

ggccatagac ggccgccagc ccagcggcga gggcaaccag cccggtgagc gtcggaaagg  15180

g                                                                  15181
```

<210> SEQ ID NO 10
<211> LENGTH: 707
<212> TYPE: DNA
<213> ORGANISM: Mentha piperita
<220> FEATURE:
<221> NAME/KEY: terminator
<222> LOCATION: (1)..(707)

<400> SEQUENCE: 10

```
ctgctttaat gagatatgcg agacgcctat gatcgcatga tatttgcttt caattctgtt     60

gtgcacgttg taaaaaacct gagcatgtgt agctcagatc cttaccgccg gtttcggttc    120

attctaatga atatatcacc cgttactatc gtatttttat gaataatatt ctccgttcaa    180

tttactgatt gtaccctact acttatatgt acaatattaa aatgaaaaca atatattgtg    240

ctgaataggt ttatagcgac atctatgata gagcgccaca ataacaaaca attgcgtttt    300

attattacaa atccaatttt aaaaaaagcg gcagaaccgg tcaaacctaa aagactgatt    360

acataaatct tattcaaatt tcaaaaggcc ccaggggcta gtatctacga cacaccgagc    420

ggcgaactaa taacgttcac tgaagggaac tccggttccc cgccggcgcg catgggtgag    480

attccttgaa gttgagtatt ggccgtccgc tctaccgaaa gttacgggca ccattcaacc    540

cggtccagca cggcggccgg gtaaccgact tgctgccccg agaattatgc agcatttttt    600

tggtgtatgt gggccccaaa tgaagtgcag gtcaaacctt gacagtgacg acaaatcgtt    660

gggcgggtcc agggcgaatt ttgcgacaac atgtcgaggc tcagcag                 707
```

-continued

```
<210> SEQ ID NO 11
<211> LENGTH: 30
<212> TYPE: DNA
<213> ORGANISM: Mentha piperita
<220> FEATURE:
<221> NAME/KEY: primer_bind
<222> LOCATION: (1)..(30)
<223> OTHER INFORMATION: Primers for cloning MPTPS4 gene in
      Overexpression vector (pHANNIBAL) MPTPS4_F_oe_Eco

<400> SEQUENCE: 11

agaattcatg gaaatttatt ccccagttgt                                       30


<210> SEQ ID NO 12
<211> LENGTH: 29
<212> TYPE: DNA
<213> ORGANISM: Mentha piperita
<220> FEATURE:
<221> NAME/KEY: primer_bind
<222> LOCATION: (1)..(29)
<223> OTHER INFORMATION: Primers for cloning MPTPS4 genein
      Overexpression vector (pHANNIBAL) MPTPS4_R_oe_Bam

<400> SEQUENCE: 12

ggatcctcaa attgcgatgg ggtcgacga                                        29
```

We claim:

1. A method for expressing increasing viridiflorol content in Lamiaceae plant tissues, said method comprising the following steps:

a) isolating the MPTS4 gene of SEQ ID NO:4 from *Mentha* piperita;

b) cloning the MPTPS4 gene obtained at step (a) into a pHANNIBAL vector to generate the cassette of SEQ ID NO:8;

c) re-cloning the cassette obtained at step (b) into a pART27 binary vector system to obtain a vector comprising SEQ ID NO:9; and d) transforming the vector obtained at step (c) into *Agrobacterium tumefaciens*, then further transfecting it into Lamiaceae plant tissues to produce Lamiaceae plant tissues exhibiting increased viridiflorol content compared to Lamiaceae plant tissues that are transfected with a control pART27 binary vector system that does not comprise the cassette of SEQ ID NO:8.

2. A transgenic plant tissue prepared by the method according to claim 1.

3. A composition comprising the transgenic plant tissue according to claim 2, wherein the composition is a perfumery, a cosmetic, a toiletry, or a drug.

4. A composition comprising the transgenic plant tissue according to claim 2, wherein the composition is a sanitation product.

* * * * *